(12) United States Patent
Malonek et al.

(10) Patent No.: US 6,292,704 B1
(45) Date of Patent: Sep. 18, 2001

(54) HIGH CAPACITANCE MYOCARDIAL ELECTRODES

(75) Inventors: Dov Malonek, Liryat Tivon; Nissim Darvish, Haifa, both of (IL)

(73) Assignee: Impulse Dynamics N. V., Curacao (AN)

( * ) Notice: Subject to any disclaimer, the term of this patent is extended or adjusted under 35 U.S.C. 154(b) by 0 days.

(21) Appl. No.: 09/384,834

(22) Filed: Aug. 27, 1999

Related U.S. Application Data

(60) Provisional application No. 60/135,864, filed on May 25, 1999.

(51) Int. Cl.$^7$ ........................................ A61N 1/05
(52) U.S. Cl. ................................................ 607/121
(58) Field of Search .................... 607/121, 122, 607/123

(56) References Cited

U.S. PATENT DOCUMENTS

| | | |
|---|---|---|
| 4,554,922 | 11/1985 | Prystowsky et al. . |
| 5,205,284 | 4/1993 | Freeman . |
| 5,385,579 | 1/1995 | Helland . |
| 5,654,030 | 8/1997 | Munshi et al. . |
| 5,871,506 | 2/1999 | Mower . |

FOREIGN PATENT DOCUMENTS

| | | |
|---|---|---|
| WO 97/25098 | 7/1997 | (WO) . |
| WO 98/10831 | 3/1998 | (WO) . |
| WO 98/10832 | 3/1998 | (WO) . |

OTHER PUBLICATIONS

Antoni H. et al., "Polarization Effects of Sinusoidal 50–Cycle Alternating Current on Membrane Potential of Mammalian Cardiac Fibers", Pflugers Arch. 314, pp. 247–291 (1970).

Primary Examiner—Scott M. Getzow
(74) Attorney, Agent, or Firm—Cowan, Liebowitz & Latman, P.C.; William H. Dippert

(57) ABSTRACT

A removable lead for applying electrical signals to excitable tissue in a body of a subject, including at least one conductive wire and at least one electrode fixed to the wire. The electrode includes a conducting substrate having a given capacitance and a given resistance and a coating applied over the conducting substrate, such that the capacitance of the electrode with the coating is at least twice the capacitance of the substrate, and the resistance of the electrode with the coating is generally equal to the resistance of the substrate.

39 Claims, 2 Drawing Sheets

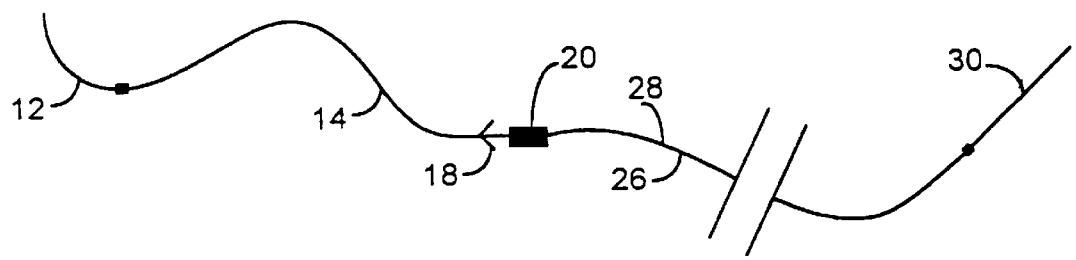
FIG. 1
FIG. 2
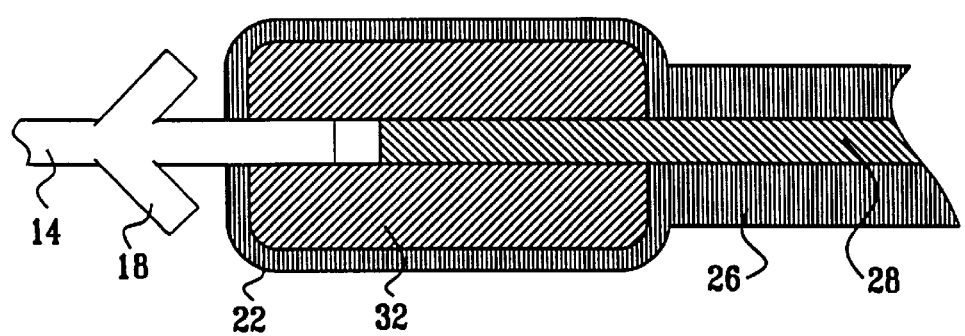

HIGH CAPACITANCE MYOCARDIAL ELECTRODES

CROSS-REFERENCE TO RELATED APPLICATION

This application is based upon U.S. Provisional Patent Application No. 60/135,864, filed May 25, 1999.

FIELD OF THE INVENTION

The present invention relates generally to electrodes, and specifically to electrodes intended for implantation in the heart.

BACKGROUND OF THE INVENTION

Implantable electrodes are known in the art to suffer from problems of corrosion, specifically faradic effects, due to, inter alia, high energy transfer across the electrodes. When implantable electrodes are used as myocardial pacing electrodes, the faradic effects manifest themselves as electrode corrosion and dangerous build-up of metal deposits in the myocardial tissue contacting the electrode. Attempts have been made in the prior art to reduce the corrosion problem by using specific inert conductors as a substrate, and covering the substrate with different types of corrosion-resistant or corrosion-reducing coatings.

U.S. Pat. No. 5,654,030, to Munshi and Bonnerup, which is incorporated herein by reference, describes a method for making implantable electrodes for cardiac stimulation. The method comprises coating a cleaned valve metal surface with one or more metal oxides selected from the oxides of ruthenium, iridium, titanium, and tantalum. (Valve metals are titanium, tantalum, niobium, hafnium, zirconium, and tungsten.) The electrodes are intended for permanent implantation, i.e., implantation over a time period of the order of years, and can be removed only by an invasive procedure.

The inventors state that stimulation requires that an electric field of adequate field strength and current density be imposed on the excitable myocardial tissue in the vicinity of the electrode to initiate rhythmic contractions. The minimum electrical pulse necessary to produce such contractions is referred to as the stimulation threshold, and the inventors define an electrode efficiency by saying that the greater the efficiency of the electrode to generate contractions, the smaller is the amplitude and/or duration of the pulse required to exceed the threshold. The inventors further state that in all types of stimulation electrodes, the electrode itself must be both chemically corrosion resistant and mechanically stable enough to withstand chronic application, that it must possess a high "charge capacity," and that it must also inject a substantial level of electric charge into the tissue to be stimulated.

U.S. Pat. No. 5,385,579, to Helland, which is incorporated herein by reference, describes a myocardial electrode formed from titanium, platinum, or platinum iridium which is intended for permanent implantation. The electrode may be coated with a particle coating intended to enhance electrical efficiency and to help minimize fibrotic tissue growth response. Examples of particle coatings are platinum black, metal oxides, and metal nitrides.

Temporary/removable implantable electrodes, i.e., electrodes which are intended to be implanted in excitable tissue for a time period of the order of days, are also known in the art. These electrodes are commonly used after open heart surgery, for example, and may be removed from the heart tissue without further surgery by pulling them firmly through the chest wall.

PCT patent applications PCT/IL97/00012, PCT/IL97/00235 and PCT/IL97/00236, which are incorporated herein by reference, describe apparatus and methods of excitable tissue control (referred to herein as ETC) of tissue such as cardiac muscle. The term "excitable tissue control," in the context of the present patent application and in the claims, refers to application of electrical signals that do not induce activation potentials in cardiac muscle cells. Rather, such signals affect the response of the heart muscle to the action potentials, by modulating cell contractility within selected segments of the cardiac muscle. Such signals are also referred to as "non-excitatory" signals.

Typically, ETC signals are of significantly longer duration and have a significantly higher current than excitatory electrical stimulation pulses, and so transfer substantially more energy to cardiac muscle than excitatory electrical stimulation pulses.

Myocardial stimulation, both non-excitatory and excitatory, is typically performed using either a unipolar or a bipolar mode. In the unipolar mode, one cardiac electrode with its associated lead is used as a stimulation electrode, and the current return path does not comprise a second cardiac electrode. For example, a conducting body of an implanted pacemaker could be used for the current return. In the bipolar mode, two separate electrodes, with respective associated leads, are used to provide a stimulation and a return terminal. The unipolar mode has the advantage of only requiring one electrode, but suffers from the disadvantage that because the current path is not well-defined, the method can easily be affected by external changes in conditions, such as a patient moving. The bipolar mode has the advantage of a well-defined current path, at the expense of utilizing two electrodes.

In addition to being used for stimulation, a pacing electrode may also be used as a sensing electrode, in order to measure electric potentials at the site where the electrode has been positioned.

SUMMARY OF THE INVENTION

It is an object of some aspects of the present invention to provide improved electrodes for use in excitable tissue control (ETC) of the heart.

It is a further object of some aspects of the present invention to provide methods for reducing harm to tissue that is temporarily implanted with removable electrodes.

It is yet a further object of some aspects of the present invention to provide methods for reducing wear of electrodes used in ETC.

In some preferred embodiments of the present invention, a removable electrode for excitable tissue control (ETC) of the heart is positioned intramyocardially, primarily for the purpose of delivering non-excitatory electrical signals to the myocardium of a patient. The ETC signals are typically used to increase the stroke volume of the patient's heart, or otherwise to promote recovery of the heart following surgery or other trauma, as described in the above-mentioned PCT patent applications and in corresponding U.S. patent applications Ser. Nos. 09/101,723, 09/254,902 and 09/254,900, which are assigned to the assignee of the present patent application and are incorporated herein by reference. A distal needle, which is preferably coupled to the electrode by a suture thread, is passed through the myocardium during surgery, so as to embed the electrode in the myocardium. The electrode is connected to an insulated conducting lead, which is pulled out to a position external to the body of the patient. The lead couples the electrode to a control unit used to generate the ETC signals. After the electrode has been used, typically after a period of days, the electrode is removed through the chest wall by pulling the conducting lead attached to the electrode, as is known in the art.

In preferred embodiments of the present invention, the electrode is made from inert material, such as platinum-iridium, coated by an inert, high-capacitance material, such as iridium oxide. In this application and in the claims, the term "high-capacitance material" refers to any material which when coated on an electrode, substantially increases the measured electrical capacitance of the electrode without substantially increasing the measured electrical resistance of the electrode. The increased capacitance of the electrode consequently increases an RC time constant of the electrode compared to electrodes that are presently used intramyocardially. Preferably, the RC time constant is at least 10 ms, and more preferably greater than 50 ms. The high capacitance, while generally impractical for pacing signals, enables the electrode to be used for delivering ETC signals by capacitive energy transfer without harm to the myocardial tissue, and without degradation of the electrode, over the time period during which the electrode is in contact with the myocardium.

In some preferred embodiments of the present invention, a plurality of electrodes, preferably coated as described above, are each connected to a respective insulated conducting wire, and the wires are combined in a single lead. The electrodes are positioned laterally along the lead so as to be electrically isolated from each other. After implantation, most preferably temporary implantation, within the myocardium, the electrodes may be used for ETC or excitatory (pacing) stimulation in a bipolar mode, and/or for sensing. The use of the single lead for implanting the plurality of electrodes in the myocardium reduces the number of sutures which are needed for the implantation procedure and hence lessens the trauma associated with the procedure.

There is therefore provided, in accordance with a preferred embodiment of the present invention, a removable lead for applying electrical signals to excitable tissue in a body of a subject, including:

at least one conductive wire; and at least one electrode fixed to the wire, the electrode including a substrate having an initial capacitance and initial resistance, which substrate is treated to increase the capacitance thereof such that the capacitance of the electrode following the treatment is at least twice the initial capacitance while the resistance of the electrode following the treatment is generally equal to the initial resistance.

Preferably, the lead includes a coating over the substrate, the coating being formed by the treatment.

Preferably, the electrode is implanted in the tissue by a surgical procedure and is removable from contact with the tissue without a further surgical procedure.

Preferably, the at least one electrode includes a plurality of electrodes, and the at least one wire includes a corresponding plurality of wires to which the electrodes are respectively fixed, such that the electrodes are laterally spaced on the lead and electrically insulated from one another.

Preferably, the substrate includes a material selected from the group of platinum, platinum-iridium, titanium and carbon.

Alternatively, the substrate includes a distal portion of the wire.

Preferably, the coating includes a high-capacitance material selected from the group of iridium oxide, titanium nitride, pyrolytic carbon, and activated carbon.

Preferably, a ratio of the capacitance of the electrode following the treatment to the initial capacitance of the substrate is in the range 2–400.

Preferably, an RC time response of the lead, when the electrode is inserted into the tissue, is greater than 10 ms.

Alternatively, a ratio of the capacitance of the electrode following the treatment to the initial capacitance of the substrate is in the range 10–400.

Alternatively, an RC time response of the lead, when the electrode is inserted into the tissue, is greater than 50 ms.

Preferably, the excitable tissue includes myocardial tissue.

Preferably, the at least one electrode senses an activation of the myocardial tissue.

Preferably, the electrical signals applied by the lead include excitable tissue control (ETC) signals.

Preferably, the ETC signals are applied to enhance hemodynamic performance of a heart including the myocardial tissue following surgery.

Preferably, the lead includes:

a surgical needle, coupled to the at least one electrode;. which needle is passed through the myocardial tissue to introduce the electrode into the tissue; and an anchor, which fixes the at least one electrode in a desired position in the tissue.

Preferably, the at least one wire passes out through the chest wall of the subject and is pulled to remove the electrode from the body.

There is further provided, in accordance with a preferred embodiment of the present invention, a lead for applying electrical signals to myocardial tissue in the heart of a subject, including:

at least one conductive wire; and at least one electrode fixed to the wire for insertion into the myocardial tissue, the electrode including a substrate which is treated such that an RC time response of the lead, when the electrode is inserted into the tissue, is greater than 10 ms.

Preferably, the lead includes a high-capacitance coating which is formed on the electrode when the substrate is treated.

Preferably, the at least one electrode is removable from contact with the myocardial tissue without a surgical procedure.

Preferably, the at least one electrode includes a plurality of electrodes, and the at least one wire includes a corresponding plurality of wires to which the electrodes are respectively fixed, such that the electrodes are laterally spaced on the lead and electrically insulated from one another.

Preferably, the plurality of electrodes are laterally spaced by a distance in the range 1 mm–3 mm.

Preferably, a diameter of at least one of the plurality of electrodes is in the range 0.5 mm–1.5 mm.

Preferably, a length of at least one of the plurality of electrodes is in the range 1 mm–5 mm.

Alternatively, the electrical signals applied by the lead include excitable tissue control (ETC) signals.

Preferably, the electrode includes a local activation sensor.

Preferably, the RC time response of the lead is greater than 50 ms.

Preferably, the excitable tissue includes myocardial tissue.

There is further provided, in accordance with a preferred embodiment of the present invention, a method for forming a lead for applying electrical signals to excitable tissue in a body of a subject, including:

forming an electrode from a conducting substrate having a given capacitance and resistance and which is fixed to a conductive wire; and applying a treatment to the conducting substrate, such that the capacitance of the electrode after the treatment is at least twice the capacitance of the substrate, and the resistance of the electrode after the treatment is generally equal to the resistance of the substrate.

Preferably, applying the treatment to the substrate includes applying a coating to the substrate.

Preferably, the electrode is implantable in the tissue by a surgical procedure and is subsequently removed from contact with the tissue without a further surgical procedure.

Preferably, the conducting substrate includes a material selected from the group of platinum, platinum iridium, titanium and carbon.

Preferably, the coating includes a high-capacitance material selected from the group of iridium oxide, titanium nitride, pyrolytic carbon, and activated carbon.

Preferably, a ratio of the capacitance of the electrode to the capacitance of the substrate is in the range 2 –400.

Alternatively, a ratio of the capacitance of the electrode to the capacitance of the substrate is in the range 10–400.

Preferably, the excitable tissue includes myocardial tissue.

There is further provided, in accordance with a preferred embodiment of the present invention, a method for treating the heart of a patient following cardiac surgery, including:

temporarily implanting an electrode in the myocardium of the heart;

exteriorizing a wire connected to the electrode through the chest wall of the patient;

applying an excitable tissue control (ETC) signal to the electrode through the wire so as to modulate contractility of the heart without generating a new action potential therein; and removing the electrode from the myocardium by pulling the wire through the chest wall.

Preferably, the method includes sensing an activation of the myocardial tissue using the electrode.

Preferably, applying the ETC signal includes applying signals so as to enhance hemodynamic performance of the heart following the surgery.

Preferably, implanting the electrode includes implanting an electrode having a high capacitance, such that an RC time response of the electrode and wire, when the electrode is inserted into the myocardium, is greater than 10 ms.

Preferably, implanting the electrode includes implanting an electrode having a high capacitance, such that an RC time response of the electrode and wire, when the electrode is inserted into the myocardium, is greater than 50 ms.

The present invention will be more fully understood from the following detailed description of the preferred embodiments thereof, taken together with the drawings, in which:

BRIEF DESCRIPTION OF THE DRAWINGS

FIG. 1 is a schematic illustration of a myocardial lead, according to a preferred embodiment of the present invention;

FIG. 2 is a schematic sectional view showing details of an electrode in the lead of FIG. 1, according to a preferred embodiment of the present invention;

DETAILED DESCRIPTION OF PREFERRED EMBODIbENTS

Figure 3:
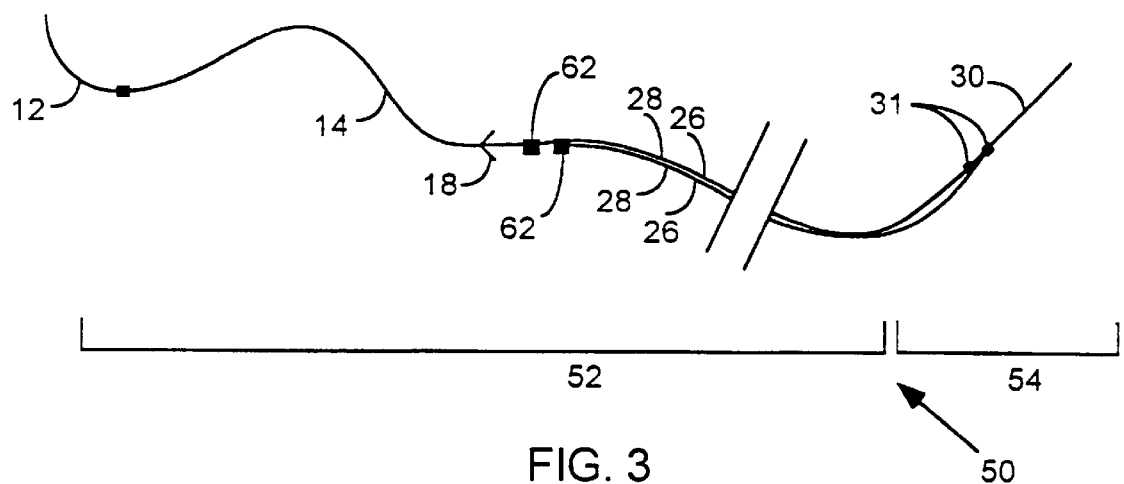
FIG. 3 is a schematic illustration of a myocardial lead, according to an alternative preferred embodiment of the present invention.

FIG. 1 is a schematic illustration of a myocardial lead 10, according to a preferred embodiment of the present invention. Lead 10 comprises a curved suture needle 12 attached at its proximal end, preferably by crimping or by another suitable method known in the art, to a suture thread 14. Thread 14 has a plurality of tines 18 fixedly connected to the thread, which tines act as an anchor for temporarily fixating an electrode 20 to a myocardium of a patient, typically during open heart surgery. As described in the Background of the Invention, the use of temporary myocardial leads for post-operative pacing of the heart is known in the art, and the method of inserting lead 10 will be clear to those skilled in the application of such pacing leads. Israel patent application 126905, which is incorporated herein by reference, describes a multi-electrode catheter and, inter alia, methods used to insert a lead of the catheter. Alternatively, other techniques known in the art, such as thread 14 being formed at its distal end into a helical coil, may be used in place of tines 18 as a means of temporarily fixating electrode 20.

Electrode 20 is preferably used for temporary treatment of the myocardium by application of ETC signals thereto, typically for a period of up to two weeks following surgery. The structure of electrode 20 is described in detail hereinbelow. A conducting wire 28 electrically connects electrode 20 to a straight conducting needle 30, preferably constructed from an inert metal, such as stainless steel. Wire 28 is covered with a biocompatible insulating coating 26, as is known in the art.

To implant electrode 20 during a cardiac surgical procedure, distal needle 12 is inserted to the myocardium, pulling fixation tines 18 and electrode 20 behind it. Once tines 18 have passed through the cardiac tissue, and electrode 20 is correctly positioned in or on the myocardium, thread 14 is cut and needle 12 and thread 14 are removed. Wire 28 is then exteriorized to the body of the patient, and the chest wall is closed. Needle 30 is connected to a suitable signal generator (not shown), such as the signal generators shown in the above-mentioned U.S. patent applications Ser. Nos. 09/254,902 and 09/254,900.

Lead 10 is thus used for transferring ETC signals and, optionally, pacing pulses to the myocardium after coronary artery bypass graft (CABG) or other cardiac surgical procedures known in the art. Alternatively or additionally, electrode 20 is also used as a sensing electrode to detect electrical activation signals in the heart, for use by the signal generator in regulating the ETC and/or pacing signals.

After completion of the post-surgical ETC and/or pacing regimen, which typically lasts for a period of up to two weeks, needle 30 is pulled away from the chest wall, pulling wire 28 and electrode 20 along with it, so that lead 10 is removed from the myocardium and the body without the need for a further surgical procedure.

FIG. 2 is a schematic, sectional view of electrode 20, according to a preferred embodiment of the present invention, showing the electrode in greater detail than is shown in FIG. 1. Electrode 20 is preferably in the form of a tube or cylinder, approximately 5 mm long and of diameter approximately 0.5 mm. Alternatively, electrode 20 comprises stranded wire in the form of a mesh sleeve, or is in the form of a wire coil, so as to increase the active surface area of the electrode. Electrode 20 grips thread 14 at the distal end of the electrode and is connected electrically to wire 28 at the proximal end of the electrode. A substrate 32 of electrode 20 is made from inert conducting material, such as platinum-iridium, platinum, titanium, or carbon, as is known in the art. Alternatively, wire 28 and substrate 32 are both made from platinum-iridium, platinum or titanium, and substrate 32 is formed by removing insulation 26 from the distal end of wire 28 to expose an uninsulated section of the wire. Further alternatively or additionally, at least part of thread 14 may be formed from the same material as wire 28.

Substrate 32 is coated with a high-capacitance material 22 in order to reduce faradic interactions between electrode 20 and the body tissue in contact with the electrode. High-capacitance material 22 coats substrate 32 in such a way that the measured electrical capacitance of the electrode is substantially enlarged, while the electrical resistance between the electrode and tissue that it contacts is substantially unchanged, compared to the measured values before coating substrate 32. Such measurements of the capacitance and of the resistance of electrode 20 are made by measuring the voltage that develops on the electrode when ETC signals are applied to lead 10. For example, the measurements may be made by placing the electrode in saline solution, and measuring the current and the current decay responsive to a known voltage pulse.

After application of high capacitance material 22 to substrate 32, an RC time constant for build-up of the voltage on the electrode following a square wave signal is in the range 50 ms–2000 ms. These values are to be compared to time constants less than 5 ms that characterize common temporary pacing electrodes. Experimentally, increasing the time constant of the electrode in accordance with preferred embodiments of the present invention has been found to substantially reduce faradic interactions between the electrode and the body tissue in contact with the electrode. This faradic interaction is insignificant at the relatively low energy of pacing pulses and over the time periods of electrode use considered herein. Therefore, the increased capacitance and consequently long time constant of electrode 20 are unnecessary in the context of pacing alone.

ETC signals, however, typically comprise 10 to 100 times the energy of pacing pulses, so that when the signals are applied over a time period of two weeks, the faradic interaction can be substantial unless a high-capacitance electrode is used. It will be appreciated that the time constant increase from less than 5 ms to a range of 50 ms–2000 ms, while the resistance is substantially constant, corresponds to an increase in capacitance of electrode 20 by a factor in the range >10 to >400.

FIG. 3 is a schematic view of a myocardial lead 50 A for temporary myocardial sensing and/or pacing, according to an alternative preferred embodiment of the present invention. Apart from the differences described below, the operation of lead 50 is generally similar to that of lead 10 (FIG. 1), so that elements indicated by the same reference numerals in both leads 50 and 10 are generally similar in construction, in dimensions, and in operation. Lead 50 comprises two electrodes 62, two wires 28, and one needle 30. Two conducting terminals 31, insulated from each other, are fixed to the needle. Each electrode 62 is substantially similar in construction to electrode 20, as described above with reference to FIG. 2, except that each electrode 62 is preferably in the form of a ring of diameter approximately 1 mm and height approximately 1 mm.

Each electrode 62 is electrically connected to a respective wire 28 covered by insulation 26, so that each wire 28 terminates in a proximal section 54 of lead 50 with a respective terminal 31 of needle 30, as described above for lead 10 with reference to FIG. 1. Both electrodes 62 are physically fixated to the insulation of at least one of wires 28, while remaining electrically insulated from each other. Most preferably, electrodes 62 are laterally separated by about 2 mm along the wire to which they are fixated. The two wires 28 are also physically fixated to each other while remaining electrically insulated from each other, preferably by cementing their respective insulation layers 26 together, within a distal section 52 of lead 50. One of electrodes 62 is connected to suture thread 14 comprising tines 18, and suture needle 12 is connected to thread 14, as described above for lead 10. Thus, along its distal section 52, lead 50 is a single lead comprising two electrodes 62.

During a cardiac electrode implant procedure, needle 12 is used to pull tines 18 and electrodes 62 into the myocardium, as described above. Preferably, electrodes 62 are used to perform bipolar pacing and/or detection of local activation in cardiac tissue where the electrodes are located. After a period of time, electrodes 62 are removed from the myocardium as described above for electrode 20.

Figure 4:
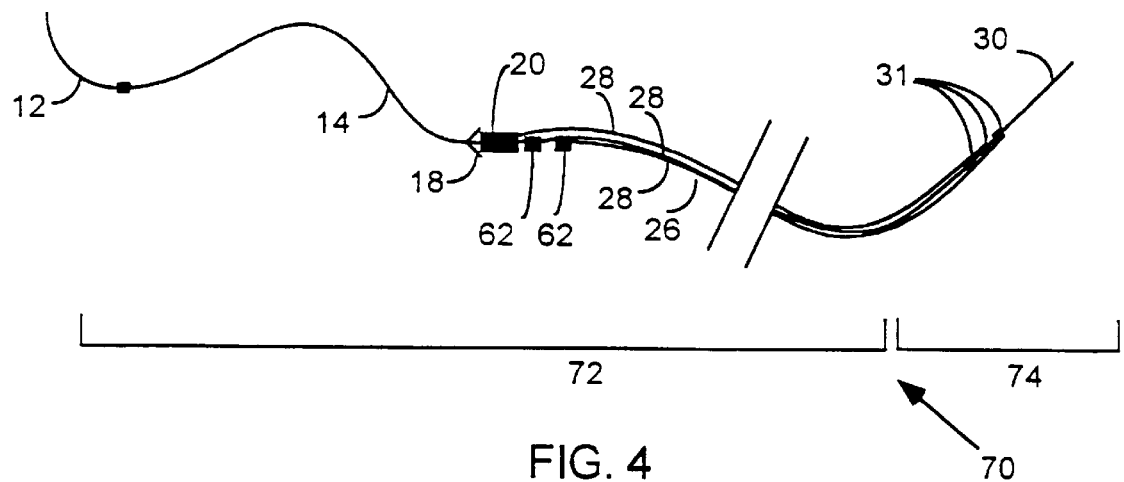
FIG. 4 is a schematic illustration of a myocardial lead, according to a further alternative preferred embodiment of the present invention.

FIG. 4 is a schematic view of a myocardial lead 70 for temporary myocardial delivery of ETC signals and pacing pulses, according to still another preferred embodiment of the present invention. Apart from the differences described below, the operation of lead 70 is generally similar to that of lead 10 (FIG. 1) and lead 50 (FIG. 3), so that elements indicated by the same reference numerals in lead 70, lead 50, and lead 10 are generally similar in construction and in operation. Lead 70 comprises ETC electrode 20 and two pacing and/or sensing electrodes 62. Each electrode is separately electrically connected to a respective insulated wire 28, as described above, so that each electrode terminates, in a proximal section 74 of lead 70, in one of three respective conducting terminals 31 fixed to needle 30. In a distal section 72 of lead 70, electrode 20 and electrodes 62 are fixedly connected to one of wires 28, as described above for lead 50, so that electrode 20 is electrically insulated from electrodes 62. Preferably, electrode 20 is connected to suture thread 14 comprising tines 18, and suture needle 12 is connected to thread 14, as described above for lead 10. Thus, along its distal section 72 lead 70 is a single lead comprising one electrode 20 and two electrodes 62.

During a cardiac electrode implant procedure, needle 12 is used to pull tines 18 and electrode 20 and electrodes 62 into the myocardium, as described above. Preferably, electrodes 62 are used to detect local activation as described above, and electrode 20 is used to deliver ETC and/or pacing pulses. Alternatively or additionally, electrode 20 may be used for local sensing. Further alternatively or additionally, one or both of electrodes 62 may be used to deliver bipolar ETC signals or pacing pulses to the myocardium. Preferably, electrode 20 is used as the anode, and one or both of electrodes 62 are used as the cathode. After conclusion of the period of temporary ETC therapy and/or pacing, lead 70 is removed from the myocardium, as described above.

While in the preferred embodiments described above, certain specific numbers and configurations of electrodes, connected on a single lead, are used for cardiac pacing and ETC, it will be appreciated that larger numbers and different configurations of electrodes can be connected to a single lead in the manner described hereinabove. Furthermore, multiple leads of this sort may be applied simultaneously to provide ETC signals at multiple sites in the heart, as described, for example, in U.S. patent application Ser. No. 09/260,769, which is assigned to the assignee of the present patent application and incorporated herein by reference. In addition, high-capacitance leads of the type described herein may be used to provide temporary stimulation when required to other types of smooth and skeletal muscle, as well. For example, such leads may be used for smooth muscle stimulation based on methods described in PCT publication Wo 99/03533, which is incorporated herein by reference. It will further be appreciated that high-capacitance leads of the type described may be produced by one or more treatment methods other than the coating method described herein, for example, by heat treatment and/or sandblasting and/or oxidation of the substrate.

It will thus be understood that the preferred embodiments described above are cited by way of example, and the full scope of the invention is limited only by the claims.

What is claimed is:

1. A removable lead for applying electrical signals to excitable tissue in a body of a subject, comprising:
    at least one conductive wire; and
    at least one electrode fixed to the wire, the electrode comprising a substrate having an initial capacitance and initial resistance, which substrate is treated to increase the capacitance thereof such that the capacitance of the electrode following the treatment is at least twice the initial capacitance while the resistance of the electrode following the treatment is generally equal to the initial resistance, such that an RC time response of the lead, when the electrode is inserted into the tissue, is greater than 10 ms.

2. A lead according to claim 1, and comprising a coating over the substrate, the coating being formed by the treatment.

3. A lead according to claim 2, wherein the coating comprises a high-capacitance material selected from the group of iridium oxide, titanium nitride, pyrolytic carbon, and activated carbon.

4. A lead according to claim 1, wherein the electrode is implanted in the tissue by a surgical procedure and is removable from contact with the tissue without a further surgical procedure.

5. A lead according to claim 1, wherein the at least one electrode comprises a plurality of electrodes, and the at least one wire comprises a corresponding plurality of wires to which the electrodes are respectively fixed, such that the electrodes are laterally spaced on the lead and electrically insulated from one another.

6. A lead according to claim 1, wherein the substrate comprises a material selected from the group of platinum, platinum-iridium, titanium and carbon.

7. A lead according to claim 1, wherein the substrate comprises a distal portion of the wire.

8. A lead according to claim 1, wherein a ratio of the capacitance of the electrode following the treatment to the initial capacitance of the substrate is in the range 2–400.

9. A lead according to claim 1, wherein a ratio of the capacitance of the electrode following the treatment to the initial capacitance of the substrate is in the range 10–400.

10. A lead according to claim 1, wherein an RC time response of the lead, when the electrode is inserted into the tissue, is greater than 50 ms.

11. A lead according to claim 1, wherein the excitable tissue comprises myocardial tissue.

12. A lead according to claim 11, wherein the at least one electrode senses an activation of the myocardial tissue.

13. A lead according to claim 11, wherein the electrical signals applied by the lead comprise excitable tissue control (ETC) signals.

14. A lead according to claim 13, wherein the ETC signals are applied to enhance hemodynamic performance of a heart comprising the myocardial tissue following surgery.

15. A lead according to claim 11, and comprising:
    a surgical needle, coupled to the at least one electrode, which needle is passed through the myocardial tissue to introduce the electrode into the tissue; and
    an anchor, which fixes the at least one electrode in a desired position in the tissue.

16. A lead according to claim 11, wherein the at least one wire passes out through the chest wall of the subject and is pulled to remove the electrode from the body.

17. A lead for applying electrical signals to myocardial tissue in the heart of a subject, comprising:
    at least one conductive wire; and
    at least one electrode fixed to the wire for insertion into the myocardial tissue, the electrode comprising a substrate which is treated such that an RC time response of the lead, when the electrode is inserted into the tissue, is greater than 10 ms.

18. A lead according to claim 17, and comprising a high-capacitance coating which is formed on the electrode when the substrate is treated.

19. A lead according to claim 17, wherein the at least one electrode is removable from contact with the myocardial tissue without a surgical procedure.

20. A lead according to claim 17, wherein the at least one electrode comprises a plurality of electrodes, and the at least one wire comprises a corresponding plurality of wires to which the electrodes are respectively fixed, such that the electrodes are laterally spaced on the lead and electrically insulated from one another.

21. A lead according to claim 20, wherein the plurality of electrodes are laterally spaced by a distance in the range 1 mm–3 mm.

22. A lead according to claim 20, wherein a diameter of at least one of the plurality of electrodes is in the range 0.5 mm–1.5 mm.

23. A lead according to claim 20, wherein a length of at least one of the plurality of electrodes is in the range 1 mm–5 mm.

24. A lead according to claim 17, wherein the electrical signals applied by the lead comprise excitable tissue control (ETC) signals.

25. A lead according to claim 17, wherein the electrode comprises a local activation sensor.

26. A lead according to claim 17, wherein the RC time response of the lead is greater than 50 ms.

27. A lead according to claim 17, wherein the excitable tissue comprises myocardial tissue.

28. A method for forming a lead for applying electrical signals to excitable tissue in a body of a subject, comprising:
    forming an electrode from a conducting substrate having a given capacitance and resistance and which is fixed to a conductive wire; and
    applying a treatment to the conducting substrate, such that the capacitance of the electrode after the treatment is at least twice the capacitance of the substrate, and the resistance of the electrode after the treatment is generally equal to the resistance of the substrate, such that an RC time response of the lead, when the electrode is inserted into the tissue, is greater than 10 ms.

29. A method according to claim 28, wherein applying the treatment to the substrate comprises applying a coating to the substrate.

30. A method according to claim 29, wherein the coating comprises a high-capacitance material selected from the group of iridium oxide, titanium nitride, pyrolytic carbon, and activated carbon.

31. A method according to claim 28, wherein the electrode is implantable in the tissue by a surgical procedure and is subsequently removed from contact with the tissue without a further surgical procedure.

32. A method according to claim 28, wherein the conducting substrate comprises a material selected from the group of platinum, platinum-iridium, titanium and carbon.

33. A method according to claim 28, wherein a ratio of the capacitance of the electrode to the capacitance of the substrate is in the-range 2–400.

34. A method according to claim 28, wherein a ratio of the capacitance of the electrode to the capacitance of the substrate is in the range 10–400.

35. A method according to claim 28, wherein the excitable tissue comprises myocardial tissue.

36. A method for treating the heart of a patient following cardiac surgery, comprising:

temporarily implanting an electrode connected to a wire in the myocardium of the heart, the electrode having a high capacitance, such that an RC time response of the electrode and wire, when the electrode is inserted into the myocardium, is greater than 10 ms;

exteriorizing the wire connected to the electrode through the chest wall of the patient;

applying an excitable tissue control (ETC) signal to the electrode through the wire so as to modulate contractility of the heart without generating a new action potential therein; and removing the electrode from the myocardium by pulling the wire through the chest wall.

37. A method according to claim 36, and comprising sensing an activation of the myocardial tissue using the electrode.

38. A method according to claim 36, wherein applying the ETC signal comprises applying signals so as to enhance hemodynamic performance of the heart following the surgery.

39. A method according to claim 36, wherein the RC time response of the electrode and wire, when the electrode is inserted into the myocardium, is greater than 50 ms.

* * * * *